（12） United States Patent
Kim et al.

(10) Patent No.: US 11,702,554 B2
(45) Date of Patent: Jul. 18, 2023

(54) COMPOUND FOR RELEASE AGENT AND METHOD FOR PREPARING THE SAME

(71) Applicant: CEKO CO., LTD., Gyeonggi-do (KR)

(72) Inventors: Hyun Joong Kim, Seoul (KR); Hong Chul Kim, Seoul (KR); Sung-Do Lee, Gyeonggi-do (KR)

(73) Assignee: CEKO CO., LTD., Gyeonggi-do (KR)

( * ) Notice: Subject to any disclaimer, the term of this patent is extended or adjusted under 35 U.S.C. 154(b) by 67 days.

(21) Appl. No.: 16/972,783

(22) PCT Filed: Aug. 26, 2020

(86) PCT No.: PCT/KR2020/011357
§ 371 (c)(1),
(2) Date: Dec. 7, 2020

(87) PCT Pub. No.: WO2021/054632
PCT Pub. Date: Mar. 25, 2021

(65) Prior Publication Data
US 2021/0261795 A1 Aug. 26, 2021

(30) Foreign Application Priority Data
Sep. 18, 2019 (KR) .................. 10-2019-0114634

(51) Int. Cl.
C09D 5/20 (2006.01)
C07C 43/174 (2006.01)
C07C 69/63 (2006.01)
C07C 271/14 (2006.01)
C07C 271/28 (2006.01)
(Continued)

(52) U.S. Cl.
CPC ............. C09D 5/20 (2013.01); C07C 43/174 (2013.01); C07C 69/63 (2013.01); C07C 271/14 (2013.01); C07C 271/28 (2013.01); C23C 14/12 (2013.01); C23C 14/24 (2013.01)

(58) Field of Classification Search
None
See application file for complete search history.

(56) References Cited

U.S. PATENT DOCUMENTS

| | | | | |
|---|---|---|---|---|
| 4,401,717 A | * | 8/1983 | Ikeda ................... | B41M 5/3375 427/151 |
| 2019/0276421 A1 | | 9/2019 | Yamamoto et al. | |
| 2021/0261795 A1 | * | 8/2021 | Kim ....................... | C09D 5/20 |

FOREIGN PATENT DOCUMENTS

| | | | | |
|---|---|---|---|---|
| EP | 0005520 | * | 10/1982 | ............... C08K 5/10 |
| JP | S58-183736 A | | 10/1983 | |

(Continued)

OTHER PUBLICATIONS

STN® registry file for the compound having the registry No. 210491-69-3 (dated Aug. 27, 1998). (Year: 1998).*

(Continued)

*Primary Examiner* — Amy C Bonaparte
(74) *Attorney, Agent, or Firm* — Harness, Dickey & Pierce, P.L.C.

(57) ABSTRACT

The present invention relates to a compound for release agent and method for preparing the same, and more specifically, to a compound for a release agent that can be coated in an ultra-thin form without thermal deformation even when heat is continuously or discontinuously applied in a continuous evaporator, and a method for preparing the same.

5 Claims, 2 Drawing Sheets

(51) Int. Cl.
*C23C 14/12* (2006.01)
*C23C 14/24* (2006.01)

(56) References Cited

FOREIGN PATENT DOCUMENTS

| | | |
|---|---|---|
| JP | H01-186843 A | 7/1989 |
| JP | H08-259976 A | 10/1996 |
| JP | H08259976 * 10/1996 | ............ B32B 27/30 |
| JP | H08-301837 A | 11/1996 |
| JP | 2011-062984 A | 3/2011 |
| JP | 2014-129517 A | 7/2014 |
| KR | 10-2015-0008696 A | 1/2015 |
| KR | 10-1541989 B1 | 8/2015 |
| KR | 10-2019-0088462 A | 7/2019 |

OTHER PUBLICATIONS

International Search Report from corresponding PCT Application No. PCT/KR2020/011357, dated Dec. 23, 2020.

* cited by examiner

| | Temperature (0.1 Å/sec) | Temperature (4.0 Å/sec) | State before deposition | State after deposition | Thickness | Contact angle | Haze |
|---|---|---|---|---|---|---|---|
| 1st | 133°C | 150°C | Powder | Liquid phase →Solid phase | 100nm | 116.3° | 0.11 |
| 2nd | 135°C | 150°C | Solid phase | Liquid phase →Solid phase | 200nm | 118.1° | 0.06 |
| 3rd | 134°C | 150°C | Solid phase | Liquid phase →Solid phase | 100nm | 117.1° | 0.08 |
| 4th | 134°C | 150°C | Solid phase | Liquid phase →Solid phase | 200nm | 116.3° | 0.05 |

FIG. 2

COMPOUND FOR RELEASE AGENT AND METHOD FOR PREPARING THE SAME

CROSS-REFERENCE TO RELATED APPLICATIONS

This application is a national phase application of PCT Application No. PCT/KR2020/011357, filed on Aug. 26, 2020, which claims the benefit and priority to Korean Patent Application No. 10-2019-0114634, filed on Sep. 18, 2019. The entire disclosures of the applications identified in this paragraph are incorporated herein by references.

FIELD

The present invention relates to a compound for a release agent and a method for preparing the same, and more specifically, to a compound for a release agent that can be coated in an ultra-thin form without thermal deformation even when heat is continuously or discontinuously applied in a continuous evaporator, and a method for preparing the same.

BACKGROUND

As the industry using plastic films increases, the demand for film coatings having additional functions has increased, and various coating technologies are required. There have been many technological advances in the continuous coating process that can be coated continuously when coating a film. Release agents using aminoalkyd resins (Korean Patent Publication No. 10-1541989), silicone release agents (Korean Patent Laid-Open Publication No. 10-2015-0008696) or fluorine-based mold release agents (Japanese Laid-Open Patent Publication No. 2014-129517) are added to resin materials and used as hard coating materials for films, or even if they are directly used as release agents, they are widely used through a wet coating process, such as release agents (Korean Patent Publication No. 10-2019-0088462) having a film thickness of 1 micron or more which is used through a wet coating process such as spin coating and photo-cured.

In the case of the wet coating process, it is difficult to form an ultra-thin film having a thickness of 1 micrometer or less, and it causes air pollution problems due to the use of a solvent. Accordingly, compared to such a wet coating process, a vacuum evaporation process capable of uniformly coating an ultra-thin film of 1 micrometer or less has been developed. The vacuum evaporation process is mainly a batch-type process, but continuous evaporation technology such as roll-to-roll, which can be continuously applied for improved productivity and efficient lamination, has also advanced.

In addition, with the development of advanced IT technology, a complex continuous evaporation process has been introduced, such as continuously coating or releasing a display substrate or a circuit board. For example, a release layer for easily removing a subsequent functional coating layer needs a function of vapor deposition coating without deformation even if heat is continuously or discontinuously applied in a vacuum evaporator. However, if the existing release agent is coated by continuous evaporation, it is denatured and decomposed by heat applied during evaporation, or it is fused and cured around a heat source such as a crucible used to deposit the material. When depositing by applying heat again after cooling, it may not be reused. Since most of the release agents are in liquid form, if they exist in a liquid form in a vacuum state, they are unstable and contaminate the inside of the evaporator.

Therefore, it is necessary to develop a release agent which must have thermal stability when the release agent is continuously deposited and coated in the evaporator, must not be thermally denatured even when heating and cooling are discontinued, and is in the form of a solid powder that can be easily handled by an operator without contaminating the inside of the evaporator due to unwanted evaporation in a high vacuum state for a long period of time.

SUMMARY

Problems to be Solved

The purpose of the present invention is to provide a compound for a release agent which can easily handle chemicals and that can form an ultra-thin film in a stable solid state under vacuum, and a method for preparing the same.

Technical Means

In order to achieve the technical purpose, in the first aspect, the present invention provides a compound for a release agent comprising a structure represented by the following Formula 1:

[Formula 1]

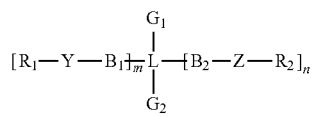

[Formula 1]
L is an aliphatic derivative or an aromatic derivative having 1 to 20 carbon atoms;
each of m and n is 0 or 1;
each of $R_1$ and $R_2$ is independently a hydrogen atom or a derivative having 1 to 40 carbon atoms and a substituted or unsubstituted aliphatic hydrocarbon group or a perfluoro alkyl group;
each of $B_1$ and $B_2$ is independently —O—, —COO—, —NHCOO— or a combination thereof;
each of $G_1$ and $G_2$ is independently H, $CH_3$, $CH_2A$ (wherein A is F, Cl, Br or I) or is omitted; and
each of Y and Z is independently an alkyl group having 1 to 6 carbon atoms.

In the second aspect, the present invention provides a compound for a release agent comprising a structure represented by the following Formula 2:

[Formula 2]

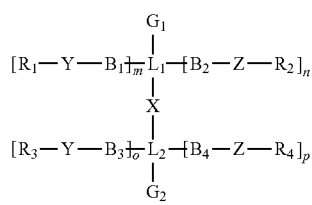

In Formula 2,
each of $L_1$ and $L_2$ is independently an aliphatic derivative or an aromatic derivative having 1 to 20 carbon atoms;
each of m, n, o and p is 0 or 1;

each of $R_1$, $R_2$, $R_3$ and $R_4$ is independently a hydrogen atom or a derivative having 1 to 40 carbon atoms and a substituted or unsubstituted aliphatic hydrocarbon group or a perfluoro alkyl group;

each of $B_1$, $B_2$, $B_3$ and $B_4$ is independently —O—, —COO—, —NHCOO— or a combination thereof;

each of $G_1$ and $G_2$ is independently H, $CH_3$, $CH_2A$ (wherein A is F, Cl, Br or I) or is omitted;

each of Y and Z is independently an alkyl group having 1 to 6 carbon atoms; and

X is —$CH_2$— or —O—.

In the third aspect, the present invention provides a release agent comprising the above compound for a release agent.

In the fourth aspect, the present invention provides a coating method for vacuum-evaporating the above release agent.

Effect of the Invention

The compound for a release agent according to the present invention improves the vulnerability of the existing release agent that is deformed by thermal deformation and chemical bonding in a continuous or non-continuous evaporator system in which continuous or intermittent deposition is continued, and has a molecular weight of 300 to 4,000 g/mol that can be deposited in a vacuum evaporator. Since it excludes functional groups capable of thermal deformation so that deposition can be performed without changing or deforming the molecular weight due to thermal decomposition or chemical bonding that occurs in the release material during deposition, it is possible to perform continuous deposition or intermittent deposition in an ultra-thin type film without deformation due to thermal decomposition or bonding, thereby increasing productivity. In addition, it is characterized in that it can be easily removed in a solvent such as alcohol, so that the release process can be easily performed.

BRIEF DESCRIPTION OF THE DRAWINGS

FIG. 2 is a result showing a change in a material state, a contact angle of a coating surface and haze after coating during deposition by heating repeatedly several times.

DETAILED DESCRIPTION

Figure 1:
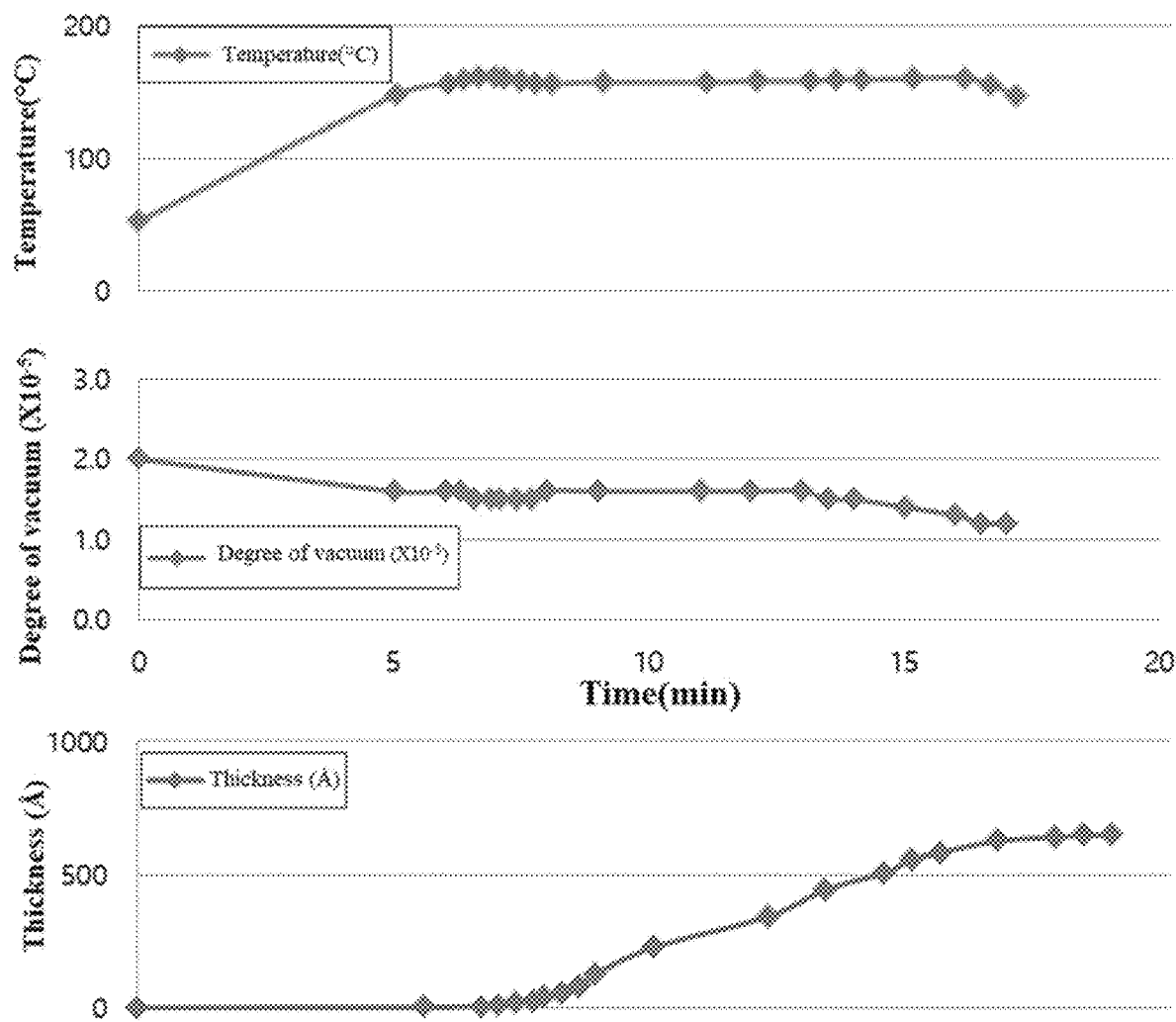
FIG. 1 is a graph showing temperature stability in a crucible, a change in thickness, and a change in a degree of vacuum in an evaporator according to time that occurs during deposition in a vacuum evaporator for Example 1 of the present invention.

The present invention is explained in more detail below.

The compound for a release agent of the present invention comprises a structure represented by the following Formula 1 or Formula 2:

[Formula 1]
$$[R_1-Y-B_1]_m-\underset{\underset{G_2}{|}}{\overset{\overset{G_1}{|}}{L}}-[B_2-Z-R_2]_n$$

In Formula 1,

L is an aliphatic derivative or an aromatic derivative having 1 to 20 carbon atoms;

each of m and n is 0 or 1;

each of $R_1$ and $R_2$ is independently a hydrogen atom or a derivative having 1 to 40 carbon atoms and a substituted or unsubstituted aliphatic hydrocarbon group or a perfluoro alkyl group;

each of $B_1$ and $B_2$ is independently —O—, —COO—, —NHCOO— or a combination thereof;

each of $G_1$ and $G_2$ is independently H, $CH_3$, $CH_2A$ (wherein A is F, Cl, Br or I) or is omitted; and each of Y and Z is independently an alkyl group having 1 to 6 carbon atoms.

[Formula 2]
$$[R_1-Y-B_1]_m-\underset{\underset{G_2}{|}}{\overset{\overset{G_1}{|}}{L_1}}-[B_2-Z-R_2]_n$$
$$\underset{}{\overset{\overset{|}{X}}{}}$$
$$[R_3-Y-B_3]_o-\underset{\underset{G_2}{|}}{\overset{\overset{}{}}{L_2}}-[B_4-Z-R_4]_p$$

In Formula 2, each of $L_1$ and $L_2$ is independently an aliphatic derivative or an aromatic derivative having 1 to 20 carbon atoms;

each of m, n, o and p is 0 or 1;

each of $R_1$, $R_2$, $R_3$ and $R_4$ is independently a hydrogen atom or a derivative having 1 to 40 carbon atoms and a substituted or unsubstituted aliphatic hydrocarbon group or a perfluoro alkyl group;

each of $B_1$, $B_2$, $B_3$ and $B_4$ is independently —O—, —COO—, —NHCOO— or a combination thereof;

each of $G_1$ and $G_2$ is independently H, $CH_3$, $CH_2A$ (wherein A is F, Cl, Br or I) or is omitted;

each of Y and Z is independently an alkyl group having 1 to 6 carbon atoms; and

X is —$CH_2$— or

The compound for a release agent of the present invention may have a total molecular weight of 300 to 4,000 g/mol.

In another aspect, the present invention provides a release agent comprising the above compound for a release agent.

In still another aspect, the present invention provides a coating method for vacuum-evaporating the above release agent.

The compound for a release agent used in the present invention or the releasing agent comprising the same, should be a single compound, not a mixed phase, so that even when deposition is repeated continuously or discontinuously, the release property can be stably implemented without thermal deformation.

In addition, vacuum evaporation can be performed in a continuous or non-continuous process using the release agent prepared according to the present invention, and when the release process is performed after depositing or coating the function to be released, it can be removed using a solvent in addition to physical methods such as drying. Although not particularly limited, the release agent may be removed using alcohols having 1 to 10 carbon atoms including methyl alcohol, ethyl alcohol, propanol, butanol, pentanol, and hexanol, and other organic solvents.

The present invention is explained in more detail through the following Synthesis Examples and Examples. However, the scope of the present invention is not limited thereby in any manner.

EXAMPLES

1. Synthesis Example 1

1,6-bis(perfluorohexylethyl urethane)hexane was prepared as follows.

In a 100 mL round bottom flask, 20 g of perfluorohexylethyl alcohol and 40 g of 1,3-bistrifluoromethylbenzene were added and stirred at room temperature for 30 minutes. 4.62 g of hexamethylene diisocyanate was added to this solution, the temperature was gradually raised to 75° C. with vigorous stirring, and a drop of dibutyl tin dilaurate catalyst was added thereto, followed by vigorous stirring for 20 hours. When it was confirmed that the isocyanate peak (2270~2290 cm$^{-1}$) disappeared from the FTIR spectrum, the mixture was cooled, the solvent and impurities were first removed using a rotary evaporator, and the solution was purified secondarily at 1 torr and 50° C. in a vacuum oven to obtain the solid content in the form of white powder. The NMR, FTIR and GC/MS spectra were consistent with the following structures.

to obtain the solid content in the form of white powder. The NMR, FTIR and GC/MS spectra were consistent with the following structures.

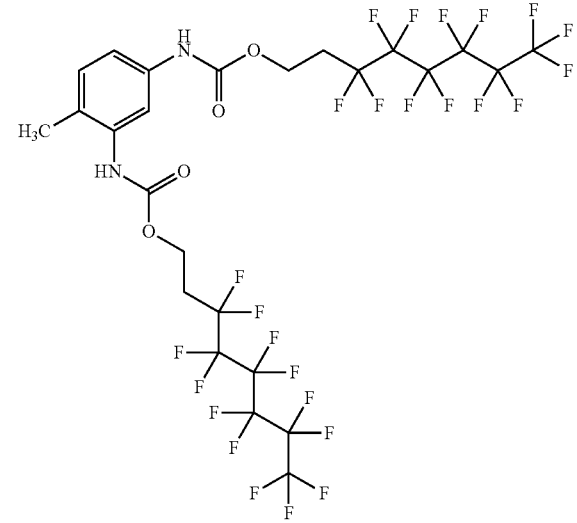

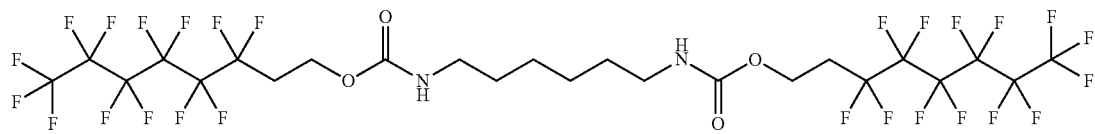 [SMILES: O=C(NCCCCCCNC(=O)OCCC(F)(F)C(F)(F)C(F)(F)C(F)(F)C(F)(F)C(F)(F)F)OCCC(F)(F)C(F)(F)C(F)(F)C(F)(F)C(F)(F)C(F)(F)F]

1,6-bis(perfluorohexylethyl urethane)hexane

2. Synthesis Example 2

2,4-bis(perfluorohexylethylurethane)-toluene was prepared as follows.

In a 100 mL round bottom flask, 20 g of perfluorohexylethyl alcohol and 40 g of 1,3-bistrifluoromethylbenzene were added and stirred at room temperature for 30 minutes. To this solution, 4.78 g of tolylene-2-4-diisocyanate was added, the temperature was gradually raised to 75° C. with vigorous stirring, and a drop of dibutyl tin dilaurate catalyst was added thereto, followed by vigorous stirring for 20 hours. When it was confirmed that the isocyanate peak (2270~2290 cm$^{-1}$) disappeared from the FTIR spectrum, the mixture was cooled, the solvent and impurities were first removed using a rotary evaporator, and the solution was purified secondarily at 1 torr and 50° C. in a vacuum oven 2,4-bis(perfluorohexylethylurethane)-toluene

3. Synthesis Example 3

1,4-bis(perfluorohexylethylurethane)benzene was prepared as follows.

In a 100 mL round bottom flask, 20 g of perfluorohexylethyl alcohol and 40 g of 1,3-bistrifluoromethylbenzene were added and stirred at room temperature for 30 minutes. To this solution, 4.41 g of 1,4-phenylenediisocyanate was added, the temperature was gradually raised to 75° C. with vigorous stirring, and a drop of dibutyl tin dilaurate catalyst was added and stirred vigorously for 20 hours. When it was confirmed that the isocyanate peak (2270~2290 cm$^{-1}$) disappeared from the FTIR spectrum, the mixture was cooled, the solvent and impurities were first removed using a rotary evaporator, and the solution was purified secondarily at 1 torr and 50° C. in a vacuum oven to obtain the solid content in the form of white powder. The NMR, FTIR and GC/MS spectra were consistent with the following structures.

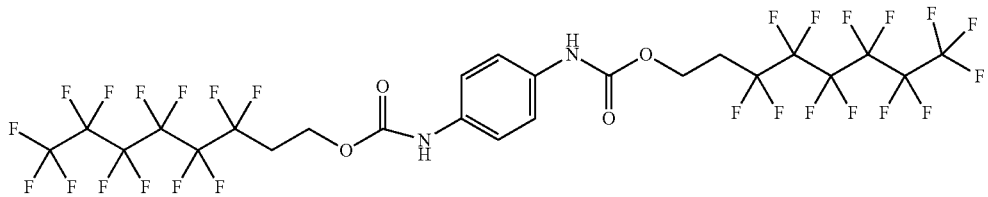 [SMILES: O=C(Nc1ccc(NC(=O)OCCC(F)(F)C(F)(F)C(F)(F)C(F)(F)C(F)(F)C(F)(F)F)cc1)OCCC(F)(F)C(F)(F)C(F)(F)C(F)(F)C(F)(F)C(F)(F)F]

1,4-bis(perfluorohexylethylurethane)benzene

4. Synthesis Example 4

Bis(4-perfluorohexylethyl urethane phenyl) was prepared as follows.

In a 100 mL round bottom flask, 20 g of perfluorohexylethyl alcohol and 40 g of 1,3-bistrifluoromethylbenzene were added and stirred at room temperature for 30 minutes. To this solution, 6.87 g of methylenediphenyldiisocyanate was added, the temperature was gradually raised to 100° C. with vigorous stirring, and a drop of dibutyl tin dilaurate catalyst was added and stirred vigorously for 20 hours. When it was confirmed that the isocyanate peak (2270~2290 cm$^{-1}$) disappeared from the FTIR spectrum, the mixture was cooled, the solvent and impurities were first removed using a rotary evaporator, and the solution was purified secondarily at 1 torr and 75° C. in a vacuum oven to obtain the solid content in the form of white powder. The NMR, FTIR and GC/MS spectra were consistent with the following structures.

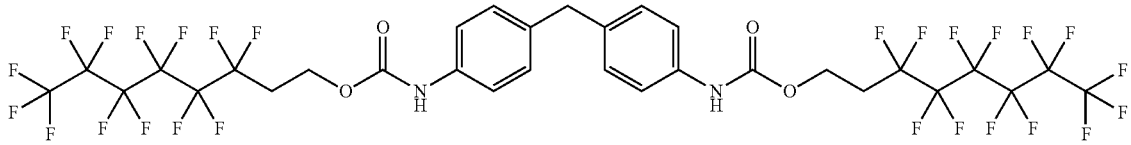 [SMILES: O=C(Nc1ccc(Cc2ccc(NC(=O)OCCC(F)(F)C(F)(F)C(F)(F)C(F)(F)C(F)(F)C(F)(F)F)cc2)cc1)OCCC(F)(F)C(F)(F)C(F)(F)C(F)(F)C(F)(F)C(F)(F)F]

Bis(4-perfluorohexylethyl urethane phenyl)methane

5. Synthesis Example 5

2,4-bis(2-octyl urethane)-toluene was prepared as follows.

To a 100 mL round-bottom flask, 10 g of tolylene-2,4-diisocyanate and 20 g of toluene were added and stirred at room temperature for 30 minutes. To this solution, 10 g of 2-octane was added, the temperature was gradually raised to 75° C. with vigorous stirring, stirred for 4 hours, and the temperature was raised to 90° C., followed by vigorously stirring for 16 hours. When it was confirmed that the isocyanate peak (2270~2290 cm$^{-1}$) disappeared from the FTIR spectrum, the mixture was cooled, the solvent and impurities were first removed using a rotary evaporator, and the solution was purified secondarily at 1 torr and 90° C. in a vacuum oven to obtain the solid content in the form of white powder. The NMR, FTIR and GC/MS spectra were consistent with the following structures.

2,4-bis(2-octyl urethane)-toluene

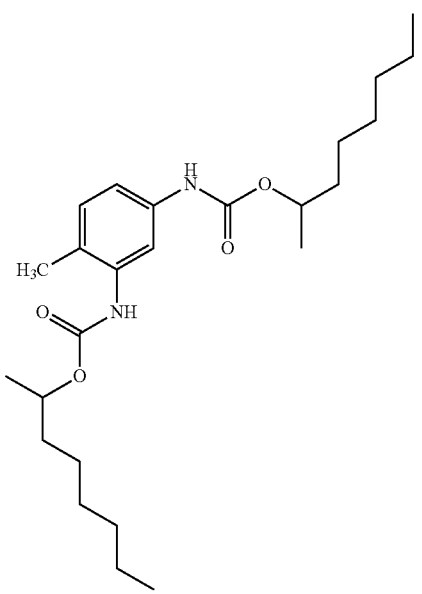 [SMILES: CCCCCCC(C)OC(=O)Nc1ccc(C)c(NC(=O)OC(C)CCCCCC)c1]

6. Synthesis Example 6

2,4-bis(1-dodecyl urethane) toluene was prepared as follows.

To a 100 mL round-bottom flask, 10 g of tolylene-2-4-diisocyanate and 20 g of toluene were added and stirred at room temperature for 30 minutes. To this solution, 21.40 g of 1-dodecanol was added, the temperature was gradually raised to 75° C. with vigorous stirring, and a drop of dibutyl tin dilaurate catalyst was added and stirred vigorously for 20 hours. When it was confirmed that the isocyanate peak (2270~2290 $cm^{-1}$) disappeared from the FTIR spectrum, the mixture was cooled, the solvent and impurities were first removed using a rotary evaporator, and the solution was purified secondarily at 1 torr and 75° C. in a vacuum oven to obtain the solid content in the form of white powder. The NMR, FTIR and GC/MS spectra were consistent with the following structures.

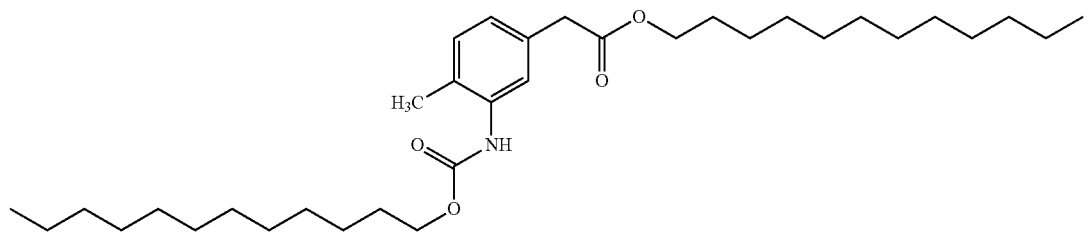 [SMILES: CCCCCCCCCCCCOC(=O)Cc1ccc(C)c(NC(=O)OCCCCCCCCCCCC)c1]

2,4-bis(1-dodecyl urethane) toluene

7. Synthesis Example 7

1,8-bis(perfluorohexylethyl ester) octane was prepared as follows.

To a 100 mL round bottom flask, 20 g of sebacic acid and 72.01 g of perfluorohexylethyl alcohol were added, the temperature was gradually raised to 130° C. with vigorous stirring, and 11.1 ml of concentrated sulfuric acid was added thereto and stirred vigorously for 20 hours. At this time, it was equipped to condense and remove water under a nitrogen atmosphere. After cooling to room temperature, 2 g of hydrotalcite was added to remove the acid and filtered to obtain a clear solution. Solvents and impurities were firstly removed from this clear solution using a rotary evaporator, and the solution was secondarily purified in a vacuum oven at 75° C. to obtain a white/light brown powdery solid. NMR, FTIR and GC/MS spectra were consistent with the following structures.

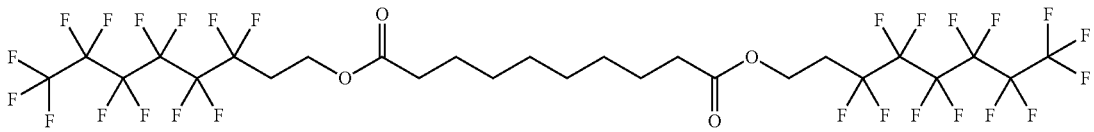 [SMILES: O=C(CCCCCCCCC(=O)OCCC(F)(F)C(F)(F)C(F)(F)C(F)(F)C(F)(F)C(F)(F)F)OCCC(F)(F)C(F)(F)C(F)(F)C(F)(F)C(F)(F)C(F)(F)F]

1,8-bis(perfluorohexylethyl ester) octane

8. Synthesis Example 8

1,2,3,4-tetra(perfluorohexylethyl ester) butane was prepared as follows.

In a 100 mL round bottom flask, 20 g of perfluorohexylethyl alcohol and 40 g of 1,3-bistrifluoromethylbenzene were added and stirred at room temperature for 30 minutes. To this solution, 3.21 g of 1,2,3,4-butanetetracarboxylic acid was added, the temperature was gradually raised to 110° C. with strong stirring, and 0.5 ml of concentrated sulfuric acid was added and stirred vigorously for 20 hours. At this time, a device capable of condensing and removing water under a nitrogen atmosphere was prepared. After cooling to room temperature, 2 g of hydrotalcite was added to remove the acid and filtered to obtain a clear solution. Solvents and impurities were firstly removed from this clear solution using a rotary evaporator, and the solution was secondarily purified in a vacuum oven at 75° C. to obtain a white/light brown powdery solid. NMR, FTIR and GC/MS spectra were consistent with the following structures.

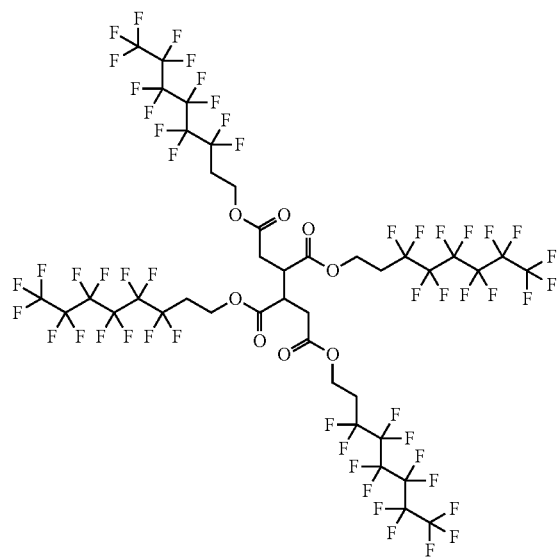 [SMILES: O=C(CC(C(=O)OCCC(F)(F)C(F)(F)C(F)(F)C(F)(F)C(F)(F)C(F)(F)F)C(CC(=O)OCCC(F)(F)C(F)(F)C(F)(F)C(F)(F)C(F)(F)C(F)(F)F)C(=O)OCCC(F)(F)C(F)(F)C(F)(F)C(F)(F)C(F)(F)C(F)(F)F)OCCC(F)(F)C(F)(F)C(F)(F)C(F)(F)C(F)(F)C(F)(F)F]

1,2,3,4-tetra(perfluorohexylethyl ester) butane

9. Synthesis Example 9

2-Perfluorohexylethyletherethyl benzene was prepared as follows.

In a 100 mL round bottom flask, 20 g of perfluorohexylethyl alcohol and 40 g of 1,3-bistrifluoromethylbenzene were added and stirred at room temperature for 30 minutes. To this solution, 4.39 g of sodium hydroxide was added, the temperature was gradually raised to 65° C. with vigorous stirring, and the mixture was stirred vigorously for 4 hours. Then, 11.18 g of (2-bromoethyl) benzene was added, the temperature was raised to 75° C., and the mixture was vigorously stirred for 5 hours. Then, it was transferred to a separatory funnel, and 100 g of hydrochloric acid having a concentration of 3 mole was added thereto, followed by addition of 100 g of acetone, followed by washing and filtering to obtain a clear solution. Solvents and impurities were firstly removed from this clear solution using a rotary evaporator, and the solution was secondarily purified in a vacuum oven at 75° C. to obtain a white/light brown powdery solid. NMR, FTIR and GC/MS spectra were consistent with the following structures.

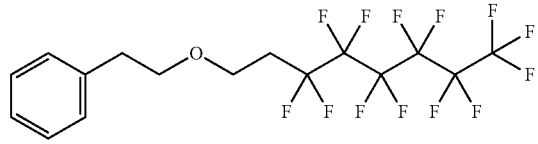 [SMILES: FC(F)(F)C(F)(F)C(F)(F)C(F)(F)C(F)(F)C(F)(F)CCOCCc1ccccc1]

2-Perfluorohexylethyletherethyl benzene

Example 1: Evaluation of Dry Vacuum Evaporation Process

Vacuum evaporation was performed using the powder prepared in Synthesis Example 2 of the above Synthesis Examples. FIG. 1 shows the relationship among a process of increasing the temperature, the change in the degree of vacuum in the vacuum evaporator during the evaporation process and the corresponding thickness increase over time by loading the powder prepared in the Synthesis Example into an effusion cell of a vacuum evaporator.

Example 2: Evaluation of Vacuum Evaporation Characteristics

Using the powder prepared in Synthesis Example 2, the process of Example 1 was repeated several times. In the process of depositing by repeated heating and cooling, the temperature at the deposition rate of 0.1 Å/sec and 4.0 Å/sec, the state before/after deposition, and the contact angle and haze at the thickness of 100 nm and 200 nm were measured and are shown in FIG. 2.

What is claimed is:
1. A compound which is any one selected from the group consisting of the following compounds:

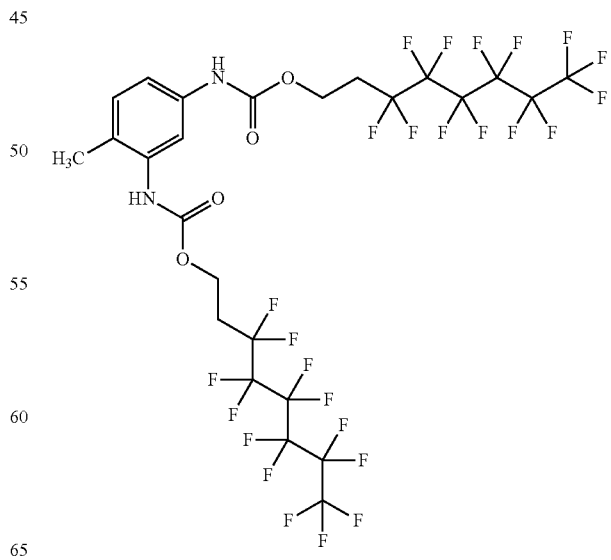

(2,4-bis(perfluorohexylethylurethane)-toluene);
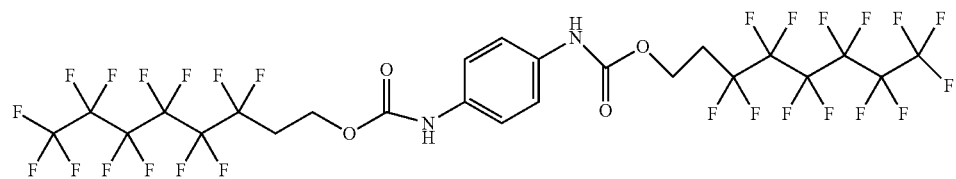 [SMILES: O=C(Nc1ccc(NC(=O)OCCC(F)(F)C(F)(F)C(F)(F)C(F)(F)C(F)(F)C(F)(F)F)cc1)OCCC(F)(F)C(F)(F)C(F)(F)C(F)(F)C(F)(F)C(F)(F)F]
(1,4-bis(perfluorohexylethylurethane)benzene);
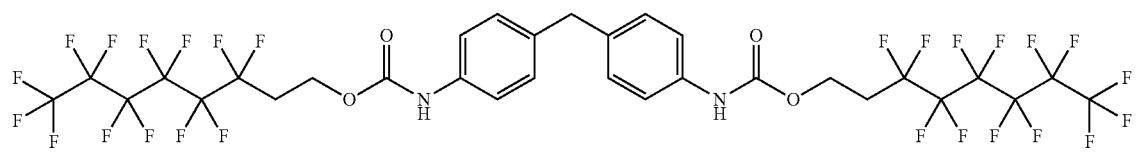 [SMILES: O=C(Nc1ccc(Cc2ccc(NC(=O)OCCC(F)(F)C(F)(F)C(F)(F)C(F)(F)C(F)(F)C(F)(F)F)cc2)cc1)OCCC(F)(F)C(F)(F)C(F)(F)C(F)(F)C(F)(F)C(F)(F)F]
(bis(4-perfluorohexylethyl urethane phenyl)methane);
(2,4-bis(2-octyl urethane)-toluene);
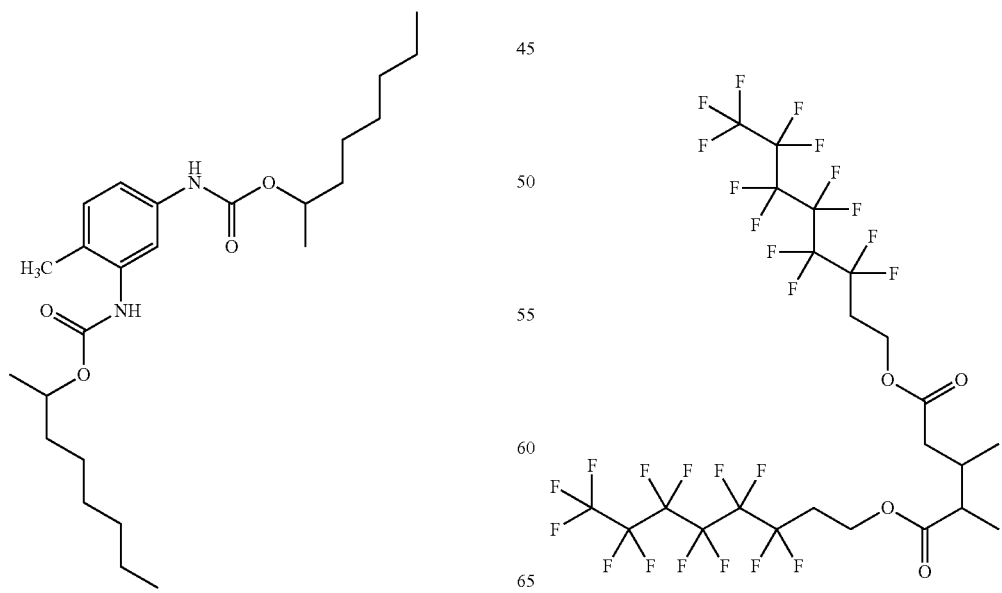

-continued

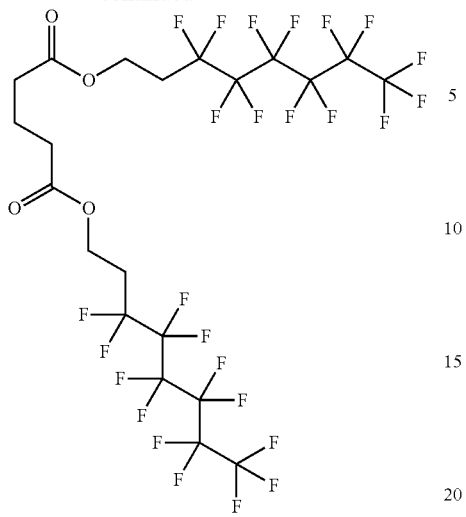

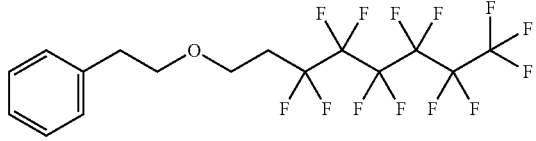 [SMILES: FC(F)(F)C(F)(F)C(F)(F)C(F)(F)C(F)(F)C(F)(F)CCOCCc1ccccc1]

(1,2,3,4-tetra(perfluorohexylethyl ester) butane); and (2-perfluorohexylethyletherethyl benzene).

2. A release agent comprising the compound according to claim 1.

3. A coating method for vacuum-evaporating a release agent, comprising:
   continuously or discontinuously vacuum-evaporating the release agent of claim 2.

4. The coating method according to claim 3, wherein the release agent is a single compound.

5. The coating method according to claim 3, wherein the vacuum-evaporated release agent is removed using alcohols or other organic solvents having 1 to 10 carbon atoms.

* * * * *